United States Patent [19]

Foll et al.

[11] Patent Number: 5,635,576

[45] Date of Patent: Jun. 3, 1997

[54] CROSSLINKABLE MATERIAL WHICH MAY BE USED IN OPTO-ELECTRONICS, PROCESS FOR PRODUCING THIS MATERIAL, AND MONOMER ALLOWING THIS MATERIAL TO BE OBTAINED

[75] Inventors: Franck Foll, Montpellier; Dominique Bosc, Lannion; Alain Rousseau; Bernard Boutevin, both of Montpellier, all of France

[73] Assignee: France Telecom, Paris, France

[21] Appl. No.: 528,109

[22] Filed: Sep. 13, 1995

[30] Foreign Application Priority Data

Sep. 16, 1994 [FR] France ................... 94 11079

[51] Int. Cl.⁶ .................. C08F 126/02; C08F 124/00
[52] U.S. Cl. ............... 526/312; 526/311; 526/270
[58] Field of Search .................. 526/311, 312, 526/270

[56] References Cited

U.S. PATENT DOCUMENTS 5,384,378  1/1995  Etzbach et al. ............. 526/256

FOREIGN PATENT DOCUMENTS

| 0271730 | 9/1988 | European Pat. Off. . |
| 0431200 | 6/1991 | European Pat. Off. . |
| 2630744 | 4/1988 | France . |
| 2246138 | 1/1992 | United Kingdom . |

OTHER PUBLICATIONS

Mandal et al, "Novel photo–crosslinked nonlinear optical polymers", Makromol. Chem., Rapid Commun. 12, 63–68 (1991).

Francis et al, "Isocyanate Cross–Linked Polymers for Nonlinear Optics", Chem. Mater. 1993, 5, 506–510.

Muller et al, "Quadratic non–linear optical properties of thermally crosslinkable polymers", Synthetic Metals, 54, (1993), 139–146.

Primary Examiner—Joseph L. Schofer
Assistant Examiner—Wu C. Cheng
Attorney, Agent, or Firm—Larson & Taylor

[57] ABSTRACT

The invention relates to a crosslinkable material containing a polymer onto which chromophores are laterally grafted, characterized in that each chromophore is within a polymer unit which corresponds to the following formula (I):

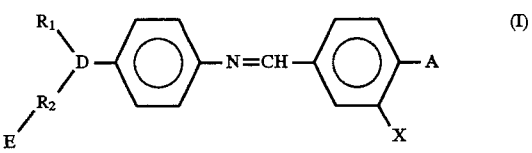

in which:

X represents a part of the polymer chain,

A is a group $-NO_2$, $-CN$, $-C(CN)=C(CN)_2$ or $-SO_2R_4$, $R_4$ being a $C_1$ to $C_6$ alkyl, D is a nitrogen, sulphur or oxygen atom, $R_1$ is a hydrogen atom or a $C_1$ to $C_6$ alkyl if D is a nitrogen atom, or nothing if D is a sulphur or oxygen atom, $R_2$ is a $C_1$ to $C_6$ aliphatic alkyl group, and E is a group chosen from $-OH$, $-O-CO-(CH_2)_n-COOH$, $-O-W$, $-O-CO-R_3O-W$ and $-O-R_3-O-W$, n being an integer between 2 and 6, W being a photodimerizable group and $R_3$ being a $C_1$ to $C_6$ alkyl, and the said material additionally containing complementary anchoring functional groups capable of attaching themselves to E during the crosslinking.

15 Claims, No Drawings

CROSSLINKABLE MATERIAL WHICH MAY BE USED IN OPTO-ELECTRONICS, PROCESS FOR PRODUCING THIS MATERIAL, AND MONOMER ALLOWING THIS MATERIAL TO BE OBTAINED

The present invention relates to crosslinkable materials which may be used in optoelectronics, as well as to processes for producing them and to monomers which allow these materials to be obtained.

These materials may be used in particular in the field of optical telecommunications and the optical treatment of signals, for example for the generation of harmonics, frequency translation, optical memories, optical modulators, optical amplifiers, etc.

Among the various materials which may be used in optoelectronics, polymerized organic materials are of competitive performance when compared with inorganic materials such as gallium arsenide and lithium niobate.

Indeed, organic materials make it possible to manufacture multilayer integrated optical circuits by techniques which have already been tried and tested on electronic integrated circuits (in particular photolithography), in contrast with inorganic materials, which must be used in the form of monocrystals. This results in lower manufacturing costs for optical components.

Furthermore, the hybridization of organic materials is easier than for inorganic materials.

In addition, organic materials allow for much faster signal treatment than inorganic materials, on account of their markedly higher rate of change of state.

Finally, in the case where these materials are used in optical modulators, organic materials make it possible to reduce the control voltage and the length of interaction between the light wave and the control electric field, thereby enabling easier use and a greater flow of data.

The polymers which may be used in optoelectronics are generally used in the form of a film. They include a carbon skeleton onto which optically nonlinear side groups (ONLGs), or chromophores, are attached.

In order for these materials to be usable in optoelectronics, they are given nonlinear optical activity, that is to say that they are given a non-zero electrooptic coefficient. For this, the ONLGs must be oriented so as to render the medium non-centrosymmetric. This, incidentally, does not exclude use of these materials in linear optics (read only memory in particular).

The orientation of ONLGs is done using a polarizing electric field perpendicular to the polymer film, at a voltage in general of the order of 100 V/µm of film thickness or greater, while the material is heated at a temperature in the region of, or slightly above, its glass transition temperature.

When the material is cooled to a temperature below its glass transition temperature, the ONLGs retain their orientation imposed by the electric field. However, little by little the ONLGs lose this orientation with time, and do so all the more rapidly the lower their glass transition temperature. Since the glass transition temperature is never very high, the polymer material thus has nonlinear optical properties that are unstable with time.

In addition, a rise is generally seen in the temperature of the optical components during their use, which further accelerates the process of orientation relaxation of the ONLGs.

In order to overcome this instability, it has been attempted to block the ONLGs, after they have been oriented, by chemical bonds.

Thus, it was endeavoured to block ONLGs by involving them in the polymerization process, while maintaining an orienting electric field during the polymerization. However, it is particularly difficult to control simultaneously the polymerization and the orientation of the ONLGs under the effect of the electric field, in the region of the glass transition temperature. In addition, the ONLG concentrations which may thus be obtained are relatively low.

Moreover, document FR-A-2,630,744 discloses a polymer material which may be used in nonlinear optics, in which the ONLGs are maintained oriented by crosslinking of the polymer, which is performed during application of an electric field for polarization of the ONLGs, after polymerization. However, the crosslinking is obtained by bonds between the carbon skeletons of the polymerized chains and not by chemical bonds which involve the ONLGs directly. Consequently, the mobility of the ONLGs, although hampered by the crosslinking, is nonetheless not suppressed.

B. K. Mandal et al. (Makromol. Chem. Rapid Commun., 12, 63–68 (1991)) have proposed to dope a polymer possessing photo-crosslinkable groups with a dye which is active in nonlinear optics, which formed the ONLGs of the polymer and which possessed the same photo-crosslinkable groups at its two ends. The crosslinking thus made it possible to block the ONLGs themselves by crosslinking after polarization, but, even in the words of the authors, this system had to be optimized in order to be exploitable. In particular, the ONLG concentrations which could be obtained thereby were low.

S. Muller et al. (Synthetic Metals, 54, 139 (1993)), has disclosed a polymer which may be used in nonlinear optics, in which the ONLGs could be interlinked by heating during their polarization by an electric field. However, the electrooptic coefficients obtained were too low. Indeed, according to a plausible hypothesis, the reaction for anchoring of the ONLGs occurred before their effective orientation had taken place.

Cécil V. Francis et al. (Chem. Mater. 1993, 5, 506–510) have disclosed a material which may be used in nonlinear optics, obtained by reaction between tolonate HDT (a triisocyanate) and a chromophore which posessed a hydroxyl group at one end and an amine function at its opposite end. The chromophores were mixed with the tolonate HDT and heated to 50° C., which brought about the reaction of the amine function with certain isocyanate groups of the tolonate HDT, giving oligomers capable of forming a film. The film was then heated to 75° C. during the application of an electric field for polarization of the chromophores, which brought about the crosslinking of the film material by reaction between the hydroxyl groups of the chromophores and the remaining isocyanate groups of the tolonate HDT. However, the material obtained have a mediocre electrooptic coefficient.

The aim of the present invention is especially to propose a material of the type described above, the ONLGs of which may be stabilized after they have been oriented, in order to obtain a polymer which may be used in nonlinear optics and which has both good nonlinear optical properties and great stability at high temperature, with a sufficient ONLG concentration.

To this effect, the subject of the invention is a crosslinkable material containing a polymer which has a chain on which are laterally grafted chromophores that are active in nonlinear optics and that may be oriented under the effect of a polarizing electric field, the said chromophores each containing an anchoring functional group in order to stabilize their orientation by crosslinking, characterized in that each chromophore is within a polymer unit which corresponds to the following formula (I):

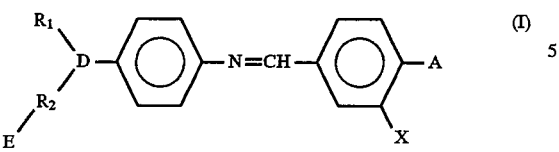

in which:

X represents a part of the polymer chain,

A is a group —$NO_2$, —CN, —C(CN)=C(CN)$_2$ or —$SO_2R_4$, $R_4$ being an optionally halogenated, and more particularly fluorinated, $C_1$ to $C_6$ alkyl group, D is a nitrogen, sulphur or oxygen atom, $R_1$ is a hydrogen atom or a $C_1$ to $C_6$ alkyl group if D is a nitrogen atom, or nothing if D is a sulphur or oxygen atom, $R_2$ is a $C_1$ to $C_6$ aliphatic alkyl group, and E is a group chosen from —OH, —O—CO—(CH$_2$)$_n$—COOH, —O—W, —O—CO—$R_3$—O—W and —O—$R_3$—O—W, n being an integer between 1 and 6, W being a photodimerizable group and $R_3$ being a $C_1$ to $C_6$ alkyl group, E constituting the anchoring functional group, and the said material additionally containing complementary anchoring functional groups capable of attaching themselves to the anchoring functional groups carried by the chromophores during the crosslinking.

In order to activate the material, that is to say, in order to give it a non-zero electrooptic coefficient, the chromophores are oriented using a polarizing electric field, and they are then blocked in their oriented position by thermochemical or photochemical crosslinking, by bonding the anchoring functional groups of the chromophores with the complementary anchoring functional groups.

In preferred embodiments of the crosslinkable material according to the invention, use is additionally made of one and/or other of the following arrangements:

E is chosen from an —OH group and an —O—CO—CH$_2$—CH$_2$—COOH group;

the anchoring functional group of the chromophore is an —O—CO—(CH$_2$)$_n$—COOH group, and the complementary anchoring functional group is chosen from the isocyanate, epoxide, hydroxyl and —SH groups, the crosslinking then being triggered by heating during the application of a polarizing electric field;

E is an —OH group, and the complementary anchoring functional group is an isocyanate, carboxylic acid or acid chloride group, the crosslinking also being triggered by heating during the application of a polarizing electric field;

E is a group chosen from —OW, —O—CO—$R_3$—O—W and —O—$R_3$—O—W, W being a photodimerizable group chosen from:

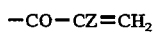

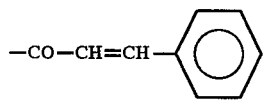

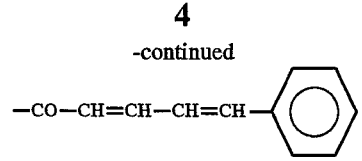

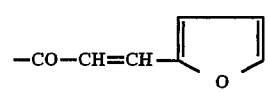

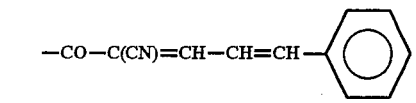

Z being a hydrogen, fluorine or chlorine atom or a methyl group, and the complementary anchoring functional group containing a photodimerizable group identical to the group W, the crosslinking then being triggered by insolation, directly after the application of a polarizing electric field and after the material has returned to room temperature, at a temperature very much below its glass transition temperature, or optionally by heating during the application of the polarizing electric field in the case of —CO—C(Z)=CH$_2$;

D is a nitrogen atom and $R_1$ is a $C_1$ to $C_6$ alkyl group or a hydrogen atom;

each chromophore is within a polymer unit which corresponds to the following formula (II):

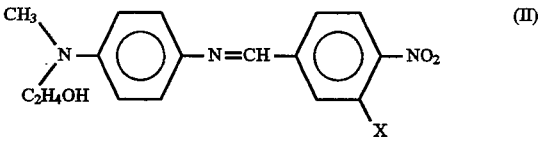

X is chosen from: the acrylate family, the α-haloacrylate family, the methacrylate family, the maleate family, the oxymethylstyrene group and the other members of the styrene family;

the chromophore is within a polymer unit which has the following formula (III):

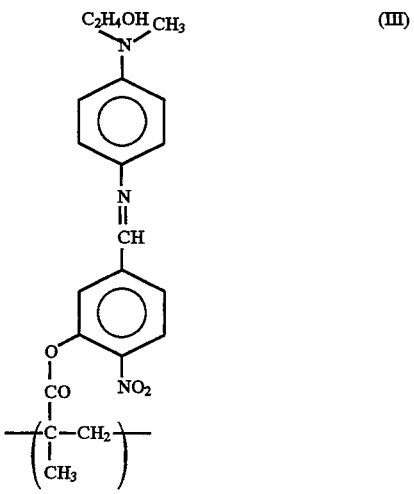

the polymer contains, besides the unit which comprises the chromophore, an additional unit, the unit which comprises the chromophore representing a molar proportion of between 10 and 50% of the polymer units, it being possible for this additional unit to serve towards adding together the thermomechanical properties of the material, as well as its optical properties, by means of concentration of the chromophores;

the additional unit is chosen from the acrylate or methacrylate family, from the styrene family, from the vinyl ester family, from the vinyl ether family or from the vinyl carbonate family;

the complementary anchoring functional group is within the additional unit of the polymer;

the complementary anchoring functional groups are carried by an additional polymer, one unit of which includes the complementary anchoring functional group, this additional polymer being intimately mixed with the polymer which carries the chromophores;

the complementary anchoring functional groups are carried by additional molecules which are intimately mixed with the polymer which carries the chromophores, these additional molecules each carrying two identical complementary anchoring functional groups, grafted onto a $C_1$ to $C_{10}$ alkyl or aryl radical, it being possible for each of the two complementary anchoring functional groups to react with the anchoring functional group of a chromophore.

The subject of the invention is also a crosslinked material which is active in nonlinear optics, obtained by crosslinking of a material as defined above, after polarization of its chromophores by an electric field, the crosslinking being obtained by chemical bonding between the anchoring functional groups carried by the chromophores, and the complementary anchoring functional groups.

Another subject of the invention is the use of such a crosslinked material, in a passive or active optical component.

This optical component may be of nonlinear type, for example a modulator.

Furthermore, the optical component in question may also be of linear type, and may consist in particular of an optical read only memory, or alternatively of a flat, two-dimensional guide.

In particular, when the crosslinking is photochemical, it is possible to crosslink the polymer material locally using a light beam, especially a laser beam, after polarization of the chromophores, and then to remove the polarization in the non-crosslinked zones by heating the whole material. It is thus possible to engrave information onto a flat support, for example an optical disc or a guide.

The crosslinkable polymer material described above may be obtained by polymerization or copolymerization of a monomer.

The subject of the invention is also such a monomer which is active in nonlinear optics, is polymerizable and contains an anchoring functional group, characterized in that it corresponds to the following formula (IV):

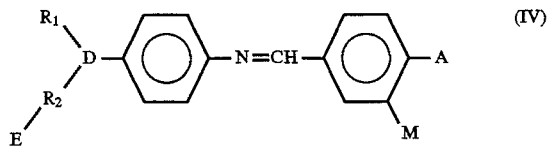

in which

A is a group $-NO_2$, $-CN$, $-C(CN)=C(CN)_2$ or $-SO_2R_4$, $R_4$ being an optionally halogenated, in particular fluorinated, $C_1$ to $C_6$ alkyl group, D is a nitrogen, sulphur or oxygen atom, $R_1$ is a hydrogen atom or a $C_1$ to $C_6$ alkyl group if D is a nitrogen atom, or nothing if D is a sulphur or oxygen atom, $R_2$ is a $C_1$ to $C_6$ aliphatic alkyl group, E is a group chosen from $-OH$, $-O-CO-(CH_2)_n-COOH$, $-O-W$, $-O-CO-R_3-O-W$ and $-O-R_3-O-W$, n being an integer between 1 and 6, W being a photodimerizable group, $R_3$ being a $C_1$ to $C_6$ alkyl group, E constituting the anchoring functional group, and M is a polymerizable group.

In preferred embodiments of this monomer, use is made of one and/or other of the following arrangements:

E is chosen from the $-OH$ and $-O-CO-CH_2-CH_2-COOH$ groups;

E is a group chosen from $-OW$, $-O-CO-R_3-O-W$ and $-O-R_3-O-W$, W being a photodimerizable group chosen from:

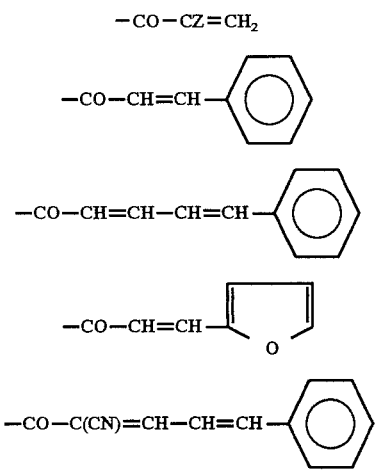

Z being a hydrogen, fluorine or chlorine atom or a methyl group;

M is a group chosen from: the acrylate family, the alpha-haloacrylate family, the methacrylate family, the maleate family, the oxymethylstyrene group and the other members of the styrene family;

the monomer corresponds to the following formula (V):

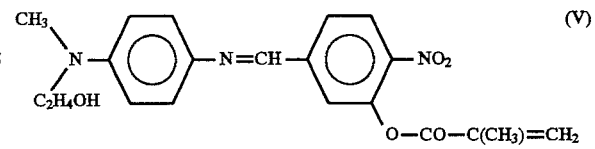

Another subject of the invention is a process for the preparation of such a monomer, characterized in that it includes a step of reaction between the compounds (VI) and (VII) below:

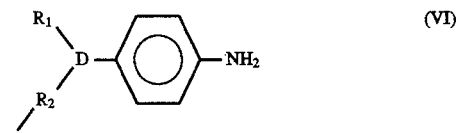

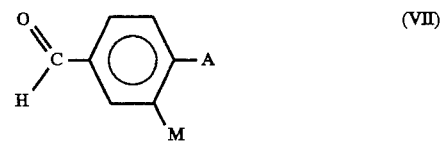

G constituting the group E if E is chosen from the $-OH$ and $-O-CO-(CH_2)_n-COOH$ groups, G being an —OH group if E is a group —O—W, G being a group —O—R₃—OH if E is a group —O—R₃—O—W, and G being a group —O—CO—R₃—OH if E is a group —O—CO—R₃—O—W.

When M is a group —O—CO—M', M' being a polymerizable group, the compound (VII) may be obtained by an esterification reaction between the acid chloride Cl—CO—M' and the following compound (VIII):

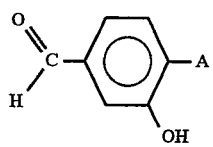
(VIII)

When E is an —O—CO—(CH₂)ₙ—COOH group, in which case the group G of the compound (VI) already constitutes the group E, G may be obtained by reaction between an OH group initially situated in place of the group G on the compound (VI) and the cyclic anhydrides of general formula (XIV):

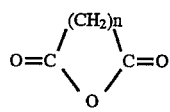
(XIV)

When E is a group —O—W and W—OH is an acid, E may be obtained by esterification between the —OH group constituting the group G and the acid chloride W—Cl, after reaction between the compounds (VI) and (VII), preferably before polymerization, except for if W is a group —CO—CZ=CH₂, where Z is a hydrogen or halogen atom or a methyl group, in which case W may be grafted on after polymerization.

When E is a group —O—R₃—O—W, E may be obtained in two steps after reaction between the compounds (VI) and (VII), preferably before polymerization, except for if W is a group —CO—CZ=CH₂, where Z is a hydrogen or halogen atom or a methyl group, in which case W may be grafted on after polymerization:

the first step is an etherification reaction between the OH function of the group G and an α-halo-ω-hydroxy compound such as: X—R₃—OH with X=Cl or Br, during the second step, the group E is obtained by esterification between the new function —O—R₃—OH obtained in place of the group G, and the acid chloride W—Cl.

When E is a group —O—CO—R₃—OW, F may be obtained in two steps after reaction between the compounds (VI) and (VII), preferably before polymerization, except for if W is a group —CO—CZ=CH₂, where Z is a hydrogen or halogen atom or a methyl group, in which case W may be grafted on after polymerization:

the first step consists in reacting the OH function of the group G with lactones of general formula (XV):

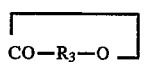
(XV)

and the second step then consists in esterifying the product obtained with W—Cl.

A specific exemplary embodiment of the invention, which is given without any limitation being implied, will now be described.

1. Synthesis of 5-formyl -2-nitrophenyl methacrylate, of formula (X):

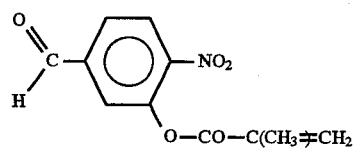
(X)

This synthesis is carried out starting with 3-hydroxy-4-nitrobenzaldehyde of formula (XI):

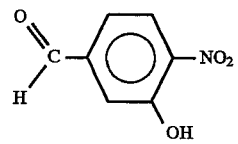
(XI)

40 ml of THF, 3 g (i.e. 17.95 mmol) of 3-hydroxy-4-nitrobenzaldehyde and 1.81 g (i.e. 17.95 mmol) of triethylamine are mixed together in a 100 cm³ two-necked round-bottomed flask fitted with a condenser.

2.06 g (19.74 mmol) of methacryloyl chloride (Cl—C(O)—C(CH₃)=CH₂) are added dropwise at room temperature.

The mixture is heated with stirring at 30° C. for 24 hours. The solution is then filtered and the filtrate is recovered by stripping off the THF under reduced pressure. The residue obtained is taken up in chloroform and is washed twice with water. The organic phase is then dried over sodium sulphate, and the solvent is stripped off. 3.3 g of pure product, which is in the form of a yellow oil, are thus obtained.

The yield is 78%.

Characteristics of the ¹H NMR spectrum in CD₃C(O)CD₃ [δ(ppm)]: 2.1 (s, 3H, —CH₃); 6 (s, 1H, C=CH₂); 6.4 (s, 1H, C=CH₂); 8 (s, 1H, HAr); 8.1 (d, 1H, HAr); 8.3 (d, 1H, HAr); 10.2 (s, 1H, —CHO).

Infrared characteristics in CHCl₃ (cm⁻¹): 1747 (—CO₂R); 1709 (—CHO); 1610 (C=CH₂); 1537 (—NO₂); 1427; 1379; 1346; 1325 (—NO₂); 1294; 1217; 1153; 952; 837.

2. Synthesis of 3-aza-3-methyl-3- (p-nitrophenyl)propanol, of formula (XII):

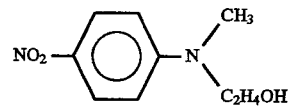
(XII)

This synthesis is carried out starting with 4-nitrobenzenesulphonyl chloride of formula (XIII):

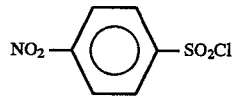
(XIII)

17.19 g (0.229 mol) of 2-methylaminoethanol (NH(CH₃)—CH₂—CH₂—OH) are added dropwise into a 500 cm³ two-necked round-bottomed flask containing 250 ml of dioxane and 25.4 g (0.114 mol) of 4-nitrobenzenesulphonyl chloride.

The reaction temperature is maintained at 100° C. for five hours, and then at room temperature for sixteen hours. The mixture is allowed to separate out by settling. The viscous residue is dissolved in 100 ml of dichloromethane and is washed twice with water. The organic phases (dichloromethane and dioxane) are washed twice with water and dried over sodium sulphate. The solvent is then stripped off on a rotary evaporator. The yellow solid obtained is washed with pentane, and turns out, on the rotovapour, to be N-[(2-hydroxyethyl)methyl]-4-nitrobenzenesulphonamide.

This product is dissolved in 20 ml of an aqueous solution containing 10% by weight of potassium hydroxide, and it is heated at 100° C. for 30 minutes. After returning to room temperature, the products are taken up twice with 150 ml of dichloromethane, and dried over sodium sulphate. The solvent is evaporated off, and the yellow solid obtained is recrystallized from methanol. The melting point of the product obtained is 109.5° C.

The reaction yield is 45%.

Characteristics of the $^1$H NMR spectrum in $CD_3C(O)CD_3$ [δ(ppm)]: 3.1 (s, 3H, —$CH_3$); 3.6 (t, 2H, N—$CH_2$); 3.8 (t, 2H, —$CH_2OH$); 6.75 (d, 2H, HAr); 8.0 (d, 2H, HAr).

Infrared characteristics in KBr ($cm^{-1}$): 3445 $cm^{-1}$ ($CH_2OH$); 2912; 1595; 1520; 1479; 1387; 1298; 1207; 1113; 1060; 833.

3. Synthesis of 3-aza-3-methyl-3-(p-aminophenyl)propanol, of formula (IX):

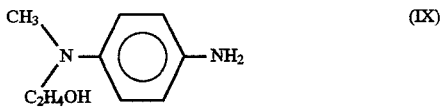

This synthesis is performed starting with 3-aza-3-methyl-3-(p-nitrophenyl)propanol.

4.6 g (23.46 mmol) of 3-aza-3-methyl-3-(p-nitrophenyl)propanol and 0.23 g (5% by weight) of 5% palladium-on-charcoal are mixed together at room temperature in 40 ml of ethanol, in a 100 cm³ two-necked flask fitted with a condenser.

10.79 g (234.6 mmol) of hydrazine monohydrate are then added slowly. The solution is then maintained at reflux overnight. The temperature is then brought to 25° C. Further small amounts of palladium-on-charcoal are added in order to destroy the hydrazine remaining in solution. The mixture is then filtered twice over filter paper, and the solvent and remaining traces of hydrazine are stripped off under reduced pressure. A proton NMR spectrum shows that the conversion of the nitro group into amine is total. 3.7 g of a clear oil are obtained, in a yield of 97%.

Characteristics of the $^1$H NMR spectrum in $CDCl_3$ [δ(ppm)]: 2.8 (s, 3H, —$CH_3$); 3.25 (t, 2H, N—$CH_2$—); 3.7 (t, 2H, —$CH_2OH$); 6.65 (d, 2H, HAr); 6.7 (d, 2H, HAr).

Infrared characteristics in KBr ($cm^{-1}$): 3450 (—$NH_2$/—OH); 3360 (—$NH_2$); 2880; 1612; 1516; 1216; 1047; 669.

4. Synthesis of 2-nitro-5-{2-aza-2-[4-N-(2-hydroxyethyl)-methylphenyl]vinyl}phenyl methacrylate, of formula (V):

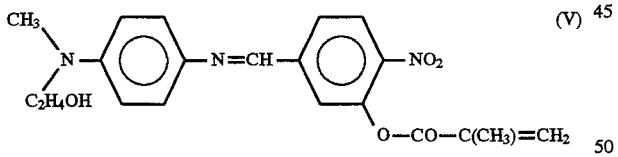

0.727 g (3.1 mmol) of 5-formyl-2-nitrophenyl methacrylate are mixed with a few mg of para-toluenesulphonic acid and a few ppm of hyrdoquinone in 25 ml of ethanol, in a 50 cm³ two-necked round-bottomed flask. A solution of 0.517 g (3.1 mmol) of 3-aza-3-methyl-3-(p-aminophenyl)propanol in 5 ml of ethanol is then added dropwise at room temperature.

The mixture is heated overnight at reflux, and the solvent is then stripped off. A proton NMR spectrum in deuterated acetone shows that the condensation reaction is total. In order to remove the traces of paratoluenesulphonic acid and hydroquinone, the mixture is chromatographed on silica, using a mixture of dichloromethane and ether (3 volume/2 volume) as eluent.

The reaction yield is 90%.

W-visible spectrophotometry gives an absorption band at 453 nm, and an absorption coefficient of 13430 l/mol/cm.

Characteristics of the $^1$H NMR spectrum in $CD_3C(O)CD_3$ [δ(ppm)]: 2.1 (s, 3H, —$CH_3$); 3.05 (s, 3H, N—$CH_3$); 3.45 (t, 2H, N—$CH_2$); 3.8 (t, 2H, —$CH_2OH$); 5.9 (s, 1H, C=$CH_2$); 6.4 (s, 1H, C=$CH_2$); 6.75 (d, 2H, HAr, J=8.9 Hz); 7.35 (d, 2H, HAr, J=8.9 Hz); 7.9 (d, 2H, HAr); 8.2 (d, 1H, HAr); 8.7 (s, 1H, —CH=N—).

Infrared characteristics in $CHCl_3$ ($cm^{-1}$): 3420 (—OH); 1745 (—$CO_2R$); 1620 (C=$CH_2$); 1591; 1568; 1516; 1319 (—$NO_2$); 1215; 1113; 839.

5. Example of the copolymerization of the monomer of formula (V) in order to obtain a polymer material which may be used in nonlinear optics:

0.35 g of the monomer of formula (V) ($9.11 \times 10^{-4}$ mol), 0.30 g of glycidyl methacrylate ($21.11 \times 10^{-4}$ mol) and 0.05 g of AIBN initiator are introduced with 7 ml of THF into a glass tube.

After a degassing operation by several vacuum-argon cycles, the mixture is maintained at 70° C. for 65 hours under argon atmosphere. The mixture is subsequently cooled and the polymer is then isolated by successive precipitations in a large volume of methanol (100 ml). The solution is filtered and the polymer is then taken up in a minimum of THF. The THF is then stripped off under reduced pressure, and 0.270 g of copolymer is thus obtained, equivalent to a yield of 41%.

The number-average Mn and weight-average Mp molecular masses are determined by steric exclusion chromatography, with polymethyl methacrylate samples as standards. Mn=3700 and Mp=7300 are found, equivalent to a polydispersity value of 1.96.

All the non-trivial starting materials mentioned in the above examples are marketed by the company Aldrich.

We claim:

1. Crosslinkable material containing a polymer which has a chain on which are laterally grafted chromophores that are active in nonlinear optics and that may be oriented under the effect of a polarizing electric field, the said chromophores each containing anchoring functional groups in order to stabilize their orientation by crosslinking, characterized in that each chromophore is within a polymer unit which corresponds to the following formula (I):

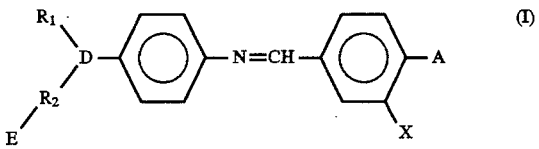

in which:

X represents a part of the polymer chain,

A is a group —$NO_2$, —CN, —C(CN)=C(CN)$_2$ or —$SO_2R_4$, $R_4$ being an optionally halogenated $C_1$ to $C_6$ alkyl group, D is a nitrogen, sulphur or oxygen atom, $R_1$ is a hydrogen atom or a $C_1$ to $C_6$ alkyl group if D is a nitrogen atom, or nothing if D is a sulphur or oxygen atom, $R_2$ is a $C_1$ to $C_6$ aliphatic alkyl group, and E is a group chosen from —OH, —O—CO—($CH_2$)$_n$—COOH, —O—W, —O—CO—$R_3$—O—W and —O—$R_3$—O—W, n being an integer between 1 and 6, W being a photodimerizable group and $R_3$ being a $C_1$ to $C_6$ alkyl group, E constituting the anchoring functional group, and the said material additionally containing complementary anchoring functional groups capable of attaching themselves to the anchoring functional groups carried by the chromophores during the crosslinking.

2. Material according to claim 1, in which E is chosen from an —OH group and an —O—CO—$CH_2$-$CH_2$—COOH group.

3. Material according to claim 2, in which the anchoring functional group of the chromophore is an —O—CO—$(CH_2)_n$—COOH group, and the complementary anchoring functional group is chosen from the isocyanate, epoxide, hydroxyl and —SH groups.

4. Material according to claim 2, in which E is an —OH group, and the complementary anchoring functional group is an isocyanate, carboxylic acid or acid chloride group.

5. Material according to claim 1, in which E is a group chosen from: —OW, —O—CO—$R_3$—O—W and —O—$R_3$—O—W, W being a photodimerizable group chosen from:

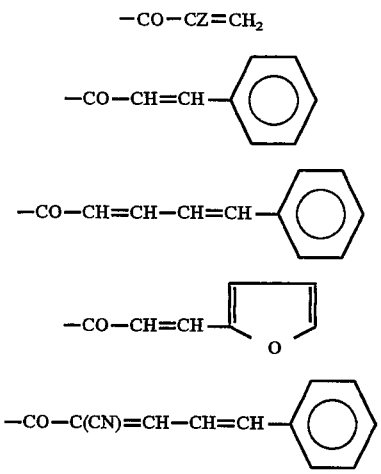

Z being a hydrogen, fluorine or chlorine atom or a methyl group and the complementary anchoring functional group containing a photodimerizable group identical to the group W.

6. Material according to claim 1, in which D is a nitrogen atom and $R_1$ is a $C_1$ to $C_6$ alkyl group or a hydrogen atom.

7. Material according to claim 1, in which each chromophore is within a polymer unit which corresponds to the following formula (II):

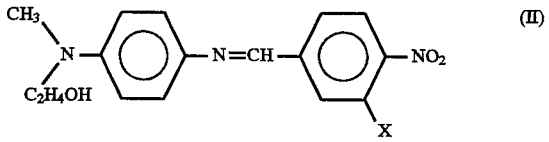

8. Material according to claim 1, in which X is chosen from: the acrylate family, the α-haloacrylate family, the methacrylate family, the maleate family, the oxymethylstyrene group and the other members of the styrene family.

9. Material according to claim 7, in which the chromophore is within a polymer unit which has the following formula (III):

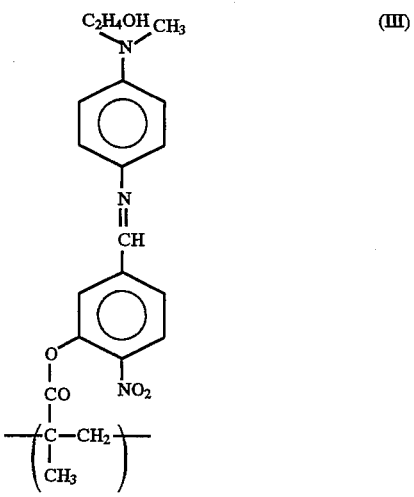

10. Material according to claim 1, in which the polymer contains, besides the unit which comprises the chromophore, an additional unit, the unit which comprises the chromophore representing a molar proportion of between 10 and 50% of the polymer units.

11. Material according to claim 10, in which the additional unit is chosen from the acrylate or methacrylate family, from the styrene family, from the vinyl ester family, from the vinyl ether family or from the vinyl carbonate family.

12. Material according to claim 10, in which the complementary anchoring functional group is within the additional unit of the polymer.

13. Material according to claim 1, in which the complementary anchoring functional groups are carried by an additional polymer, one unit of which includes the complementary anchoring functional group, this additional polymer being intimately mixed with the polymer which carries the chromophores.

14. Material according to claim 1, in which the complementary anchoring functional groups are carried by additional molecules which are intimately mixed with the polymer which carries the chromophores, these additional molecules each carrying two identical complementary anchoring functional groups, grafted onto a $C_1$ to $C_{10}$ alkyl or aryl radical, it being possible for each of the two complementary anchoring functional groups to react with the anchoring functional group of a chromophore.

15. Crosslinked material that is active in nonlinear optics, obtained by crosslinking of a material according to claim 1, after polarization of its chromophores by an electric field, the crosslinking being obtained by chemical bonding between the anchoring functional groups carried by the chromophores, and the complementary anchoring functional groups.

* * * * *